(12) United States Patent
Roesch et al.

(10) Patent No.: US 7,442,810 B2
(45) Date of Patent: Oct. 28, 2008

(54) METHOD FOR THE PRODUCTION OF DEFINED MIXTURES OF THF, BDO AND GBL BY GAS PHASE HYDROGENATION

(75) Inventors: Markus Roesch, Dienheim (DE); Rolf Pinkos, Bad Duerkheim (DE); Michael Hesse, Worms (DE); Stephan Schlitter, Limburgerhof (DE); Henrik Junicke, Mannheim (DE); Olga Schubert, Ludwigshafen (DE); Alexander Weck, Freinsheim (DE); Gunther Windecker, Ludwigshafen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 84 days.

(21) Appl. No.: 10/581,074

(22) PCT Filed: Dec. 4, 2004

(86) PCT No.: PCT/EP2004/013811

§ 371 (c)(1),
(2), (4) Date: May 31, 2006

(87) PCT Pub. No.: WO2005/058853

PCT Pub. Date: Jun. 30, 2005

(65) Prior Publication Data

US 2007/0135650 A1    Jun. 14, 2007

(30) Foreign Application Priority Data

Dec. 9, 2003    (DE) .................. 103 57 715

(51) Int. Cl.
*C07D 307/00* (2006.01)
*C07D 307/02* (2006.01)

(52) U.S. Cl. ....................... 549/295; 549/429

(58) Field of Classification Search .............. 549/325, 549/508, 429, 295; 568/864
See application file for complete search history.

(56) References Cited

U.S. PATENT DOCUMENTS 6,248,906 B1 *  6/2001  Bertola ................ 549/326
6,730,800 B2 *  5/2004  Fischer et al. ............ 549/507
6,958,404 B2 * 10/2005  Borchert et al. ......... 549/325
7,154,011 B2 * 12/2006  Hesse et al. ............. 568/864
7,271,299 B2 *  9/2007  Hesse et al. ............. 568/852

FOREIGN PATENT DOCUMENTS

| DE | 100 61 556 | 6/2002 |
| EP | 0 373 947 | 6/1990 |
| JP | 2-233631 | 9/1990 |
| JP | 2639463 | 9/1990 |
| WO | 97/43234 | 11/1997 |
| WO | 99/35136 | 7/1999 |

* cited by examiner

*Primary Examiner*—D. Margaret Seaman
*Assistant Examiner*—Nizal S Chandrakumar
(74) *Attorney, Agent, or Firm*—Oblon, Spivak, McClelland, Maier & Neustadt, P.C.

(57) ABSTRACT

A process for variably preparing mixtures of optionally alkyl-substituted BDO, GBL and THF by two-stage hydrogenation in the gas phase of $C_4$ dicarboxylic acids and/or derivatives thereof, which comprises
  a) hydrogenating in a gas phase a gas stream of $C_4$ dicarboxylic acids and/or derivatives thereof over a particular catalyst at a particular pressure and temperature to give a stream mainly containing of optionally alkyl-substituted GBL and THF,
  b) removing any succinct anhydride,
  c) converting the products remaining predominantly in the gas phase in the partial condensation, THF, water and GBL to give a stream comprising a mixture of BDO, GBL and THF,
  d) removing the hydrogen from the products and recycling it into the hydrogenation,
  e) distillatively separating the products, THF, BDO, GBL and water, if appropriate recycling a GBL-rich stream or if appropriate discharging it, and working up BDO, THF and GBL distillatively,
and setting the ratio of the products, THF, GBL and BDO, relative to one another within the range from 10 to 100% by weight of THF, from 0 to 90% by weight of GBL and from 0 to 90% by weight of BDO only by varying the temperatures in the two hydrogenation zones and also if appropriate the GBL recycle stream.

22 Claims, No Drawings

METHOD FOR THE PRODUCTION OF DEFINED MIXTURES OF THF, BDO AND GBL BY GAS PHASE HYDROGENATION

The present invention relates to a process for preparing optionally alkyl-substituted mixtures of tetrahydrofuran (THF), butanediol (BDO) and/or butyrolactone (GBL) by catalytic hydrogenation in the gas phase of substrates which are selected from the group consisting of derivatives of maleic acid and succinic acid and these acids themselves. In the context of the present invention, derivatives refer to anhydrides which, just like the acids, may have one or more alkyl substituents.

The hydrogenation of MA leads via the intermediate succinic anhydride (SA) to butyrolactone (GBL) and subsequently to THF. Overhydrogenation reactions lead to n-butanol (BuOH) and n-butane. GBL and BDO are in a pressure- and temperature-dependent equilibrium which lies toward the side of butanediol at low temperatures and high pressures. The desired product, butanediol, may react by cyclization to give THF and by overhydrogenation to give butanol and butane.

The gas phase hydrogenation of purified maleic anhydride (MA) to butyrolactone (GBL) and/or THF and the conversion of purified GBL to BDO are two reactions which have been known for many years. For the implementation of each of these catalytic reactions, the literature describes numerous catalyst systems. Depending on the selection of the catalysts and on the selected reaction parameters, such catalysts achieve different product mixtures. Processes for preparing butanediol starting from MA are likewise already known.

When GBL and BDO which have alkyl substituents are to be prepared, one possibility is to use the corresponding alkyl-substituted species of the aforementioned reactants.

For the different stages of the hydrogenation of MA to the products, THF, GBL and BDO, various catalysts are known which frequently contain chromium, especially in the case of older processes. The hydrogenation is restricted in most cases to MA as the reactant.

U.S. Pat. No. 5,149,836 discloses a multistage gas phase process for preparing GBL and THF with product selectivities variable within the limits: 15%-92% GBL and 7%-83% THF. In a first stage, a mixture of pure MA and hydrogen is passed over a catalyst which comprises copper, zinc and aluminum. This crude reaction effluent is subsequently passed over a chromium catalyst. The GBL to THF ratio is influenced by the variation of the contact time in the second reactor, the temperature and the amounts of catalyst relative to one another.

WO 99/35136 discloses a two-stage process for preparing GBL and THF, in which MA is hydrogenated in a first stage with a copper catalyst. The thus obtained reaction effluent is passed over an acidic silicon-aluminum catalyst. The proportion of GBL and BDO is 60%. A disadvantage of this process is the stiff product mix.

A process for coproducing BDO and THF starting from MA over catalysts comprising copper, chromium and manganese is disclosed in EP-A 0 373 947. According to the working examples, preference is given to using mixtures of MA and GBL, mixtures of MA and 1,4-dioxane and pure MA. In all cases, THF yields of approx. 10-15 mol % are obtained. However, a disadvantage is that exclusively mixtures of BDO and THF, but no GBL-containing mixtures are obtainable. GBL is obtained only at a low hydrogen reactant excess and at pressures close to atmospheric pressure. In addition, the catalyst hourly space velocities are so low (0.03-0.04 $kg_{MA}/l_{cat}h$) that the process appears uneconomic.

The use of a chromium-free catalyst based on mixed Cu—Al oxides is disclosed in JP 2 233 631. The aim of this invention is to carry out the hydrogenation of MA in such a way that the main products formed are THF and BDO in addition to only small amounts, if any, of GBL. This is achieved in this case by the use of the catalysts based on mixed Cu—Al oxides, and also compliance with certain reaction conditions. There are no general specifications of amounts of the oxides of Cu and Al; the examples disclosed 2 catalyst compositions, one with approx. 46% by weight of CuO and 33% by weight of $Al_2O_3$, the other with approx. 36% by weight of CuO and 47% by weight of $Al_2O_3$. According to the examples, the hydrogenation is carried out at temperatures between approx. 210 to 230° C. and GHSV values of from approx. 3200 to 9600. The hydrogen/MA ratios are at high values comparatively unfavorable for industrial processes, from 200 to 800 in the examples.

The hydrogenation of MA under conditions which correspond to those in JP 2 233 631, but using another catalyst, are disclosed in JP 2 639 463. The use of the catalyst is intended to enable the preparation of BDO and THF by hydrogenation of MA. In this case, use is made of a copper oxide/zinc oxide/aluminum oxide catalyst whose composition is not laid out quantitatively in the description. The catalysts used in the examples have a composition of 20% by weight of CuO, 43.6% by weight of ZnO and 18.1% by weight of $Al_2O_3$; 32.6% by weight of CuO, 38.1% of ZnO and 9.5% by weight of $Al_2O_3$; 24.2% by weight of CuO, 36.4% by weight of ZnO and 17.2% by weight of $Al_2O_3$; 26.4% by weight of CuO, 52.9% by weight of ZnO, 7.6% by weight of $Al_2O_3$ and 1.4% by weight of CaO; and 22.9% by weight of CuO, 44.8% by weight of ZnO and 16.3% by weight of $Al_2O_3$. Operation is generally effected in a solvent such as GBL or dioxane.

The technologies on which the above-cited publications are based use, as the reactant for the hydrogenation reactions, pre-purified MA which has generally been freed of impurities by distillation after its preparation. MA is prepared by partial oxidation of certain hydrocarbons, specifically benzene, butene mixtures and n-butane, the latter being used with preference. The crude product of the oxidation comprises, in addition to the desired MA, in particular by-products such as water, carbon monoxide, carbon dioxide, unconverted starting hydrocarbon and acetic acid and acrylic acid, these by-products being independent of the hydrocarbons used in the oxidation. Usually, the by-products are removed by complicated processes, for example by distillation as mentioned above. The purification is found to be necessary especially because the catalysts used in the hydrogenation processes generally react sensitively to such impurities. The deactivation of the catalysts is a problem even when purified MA is used, since fouling with its polymerization products results in the catalyst generally having to be regenerated within relatively short intervals which are often approx. 100 hours. The tendency toward deactivation is increased further in the presence of polymerizable impurities, for example acrylic acid. This fact is known to those skilled in the art and is also described, for example, in the patent application EP-A 322 140.

Moreover, there exist in the prior art few publications which disclose the hydrogenation of merely roughly prepurified MA.

DE 10061556 and WO 97/43234 disclose the absorption of maleic anhydride from maleic anhydride-containing gas streams which stem from the oxidation of hydrocarbons with the aid of absorbents having a boiling point at least 30° C. higher, driving maleic anhydride out of these absorbents with the aid of hydrogen and hydrogenating the maleic anhydride-containing hydrogen stream in the gas phase over a heterogeneous catalyst. In WO 97/43234, mainly BDO in addition to small amounts of GBL and THF is obtained. The hydrogenation is carried out in the gas phase at from about 150° C. to 300° C. and a pressure of from 5 bar to 100 bar. The catalysts used are promoted copper catalysts, as described in Journal of Catalysis 150, pages 177 to 185 (1994). These are chromium catalysts of the Cu/Mn/Ba/Cr and Cu/Zn/Mg/Cr type. Thus, according to the disclosure of this application, chromium catalysts are used to hydrogenate qualities of MA which have the impurities laid out above. However, the use of chromium catalysts is nowadays avoided as far as possible owing to the toxicity. In DE 10061556, THF is obtained in high yields. GBL occurs as a secondary component; BDO is not observed.

It is an object of the present invention to provide a process by which it is possible to selectively obtain, starting from MA, mixtures of BDO, GBL and THF having a defined composition, i.e. having a proportion of the three products, BDO, GBL and THF, laid down as desired by the operator of the process, in which, depending on the desired product, different amounts of BDO, GBL and THF can be obtained without altering the plant or the catalyst. This process should be operable continuously and afford very large amounts of the products of value, BDO, GBL and THF, in order thus to achieve best possible economic viability. Moreover, the catalyst should be compatible with MA which has not been prepurified in a complicated manner, for example by distillation, and, in spite of this, have high stability, i.e. not require frequent regeneration. The process should enable the variability to the operator to obtain an altered product mixture without a catalyst change, i.e. only by changing the operating parameters, in order to be able to adapt flexibly and economically to the market demands. All accessible product mixtures should be substantially SA-free, in order firstly to prevent process problems (displacements in pipelines), but secondly also to minimize yield losses. The catalyst used should be inexpensive and noble metal-free. The stressability of the catalyst should be very high. The MA should be used without solvent in the hydrogenation in order to prevent recycling of the solvent. In addition, liquid phase hydrogenations of aqueous maleic acid solutions should be avoided owing to the uneconomically high pressure and the corrosivity of the feed stream. Gas phase processes at atmospheric pressure should also be avoided, since uneconomically high gas volumes have to be moved in circulation in such processes. Multistage hydrogenations should also be realized at one pressure stage in order to achieve higher economic viabilities.

This object is achieved by a process for variably preparing mixtures of optionally alkyl-substituted BDO, GBL and THF by two-stage hydrogenation in the gas phase of $C_4$ dicarboxylic acids and/or derivatives thereof, which comprises a) in a first step in the gas phase, hydrogenating a gas stream of $C_4$ dicarboxylic acids and/or derivatives thereof over a catalyst at a pressure of from 2 to 100 bar and a temperature of from 200° C. to 300° C. in a first reactor in the presence of a catalyst in the form of shaped catalyst bodies having a volume of less than 20 mm$^3$, said catalyst from 5 to 95% by weight of oxide of copper and from 5 to 95% by weight of an oxide having acidic sites, to give a stream mainly containing of optionally alkyl-substituted GBL and THF, b) removing any succinic anhydride formed by partial condensation, c) converting the products remaining predominantly in the gas phase in the partial condensation, THF, water and GBL, under the same pressure or under a pressure reduced by the pressure drops in the hydrogenation circuit and at a temperature of from 150 to 240° C., in a second reactor over a catalyst which ≦95% by weight of CuO and from 5 to 95% by weight of one or more oxides selected from the group of ZnO, $Al_2O_3$, $SiO_2$, $TiO_2$, $ZrO_2$, $CeO_2$, MgO, CaO, SrO, BaO and $Mn_2O_3$ to give a stream comprising a mixture of BDO, GBL and THF, d) removing the hydrogen from the products and recycling it into the hydrogenation, e) distillatively separating the products, THF, BDO, GBL and water, if appropriate recycling a GBL-rich stream into the second reactor or if appropriate discharging it, and working up BDO, THF and GBL distillatively, and setting the ratio of the products, THF, GBL and BDO, relative to one another within the range from 10 to 100% by weight of THF, from 0 to 90% by weight of GBL and from 0 to 90% by weight of BDO only by varying the temperatures in the two hydrogenation zones and also if appropriate the GBL recycle stream.

In relation to the present application, the term $C_4$ dicarboxylic acids and derivatives thereof refers to maleic acid and succinic acid, each of which optionally has one or more $C_1$-$C_6$-alkyl substituents, and also the anhydrides of these optionally alkyl-substituted acids. An example of such an acid is citraconic acid. Preference is given to using the particular anhydrides of a given acid. In particular, the reactant used is MA.

The partial condensation of SA, well known per se to those skilled in the art, may also be configured as a circulation quench circuit. In this case, the reaction gases are quenched with the condenate of the partial condensation itself.

The evaporation of the GBL recycle stream from stage e), i.e. the recycled GBL or GBL/water mixture, with the GBL/THF-laden cycle gas hydrogen may be effected in a countercurrent contact apparatus, preferably a stripping column.

The partial condensation of the succinic anhydride and the evaporation of the GBL or GBL/water recycle stream may also be combined in one apparatus, preferably in a countercurrent stripping column with external quench circuit, in which case the succinic anhydride may be discharged as the bottom effluent together with residual GBL, water and high-boiling secondary components.

This process is best suited to continuous operation.

According to the invention, the gas stream leaving the second reactor is cooled to from 10 to 60° C. The reaction products are condensed out and passed into a separator. The uncondensed gas stream is removed from the separator and fed to the cycle gas compressor. A small amount of cycle gas is discharged. The reaction products which have been condensed out are withdrawn continuously from the system and fed to a workup. The by-products found in the liquid phase which has been condensed out are mainly n-butanol in addition to small amounts of propanol.

To achieve the inventive BDO, GBL and THF selectivities, it is also necessary to comply with certain reaction parameters.

An important parameter is the compliance with a suitable reaction temperature in the first reactor. One way of achieving this is by an adequately high inlet temperature of the reactants into the reactor. This is at values of from >220 to 300° C., preferably from 235 to 270° C. In order to achieve acceptable or high target product selectivity and yield, the reaction has to be carried out in such a way that there is a suitably high reaction temperature at the catalyst bed over which the actual reaction takes place. At a given pressure, hydrogen/reactant ratio and hourly space velocity, the inlet temperature can be used to establish a temperature profile over the length of the reactor, and several temperature maxima may be achieved in the first reactor. These hotspot temperatures are at values of from 240 to 310° C., preferably from 240 to 280° C. The process is carried out in such a way that the inlet temperature of the reaction gases in the first reactor is below this hotspot temperature. The first hotspot is located in the first half of the first reactor after the entry point of the reaction mixture, especially when a tube bundle reactor is present. Preferably, the first hotspot temperature is from 5 to 15° C., in particular from 10 to 15° C., above the inlet temperature. If a second hotspot occurs in the first reactor, it may be disposed at any point in the reactor and its location is shifted toward the reactor outlet by reducing the inlet temperature. The second hotspot temperature is preferably from 1 to 15° C., in particular from 2 to 10° C., above the inlet temperature. When mixtures comprising mainly THF are to be obtained, this second hotspot is preferably within the first ⅔ of the first reactor; if GBL- and BDO-containing mixtures are to be obtained preferentially, the second hotspot is disposed in the last third, in particular at the reactor outlet of the first reactor.

When the hydrogenation is carried out below the minimum temperatures of the inlet or hotspot temperature, deactivation of the catalyst as a result of fouling with succinic acid, fumaric acid and/or SA is observed in the course of the hydrogenation. In contrast, when hydrogenation is effected using MA as the reactant above the maximum temperatures of the inlet or hotspot temperature, the GBL and THF yield and selectivity fall to unsatisfactory values. In this case, it is the increased formation of n-butanol and n-butane that is observed, i.e. the products of further hydrogenation.

A further important parameter is the compliance with a suitable inlet temperature in the second reactor. This is at values between 150° C. and 270° C., preferably from 175° C. to 195° C. When the hydrogenation is carried out below the minimum temperatures of the inlet temperature, the amount of GBL rises. The catalyst loses activity. Moreover, it is to be expected below the minimum temperature that the starting materials will condense out and the copper catalyst will be permanently damaged by water. When hydrogenation is effected above the maximum temperatures of the inlet temperature, the BDO yield and selectivity fall to unsatisfactory values. However, by-product formation resulting from overhydrogenation to n-butanol and n-butane is to be observed to an increased extent at higher temperature.

The temperature increase of the gas stream in the second reactor must not exceed 90° C., the temperature increase must preferably not exceed 40° C., and in particular not be more than 20° C. Here too, excessively high temperature increases lead to overhydrogenation reactions and a (BDO, THF+GBL) selectivity loss.

The pressure range is of crucial importance for the BDO yield. In combination with the temperature and the amount of hydrogen, care has to be taken that all starting materials are in the gas phase.

In the hydrogenation, a pressure of from 2 to 100 bar, preferably a pressure of from 2 to 60 bar and more preferably a pressure of from 15 to 35 bar, is selected. In this pressure range, the GBL to BDO ratio in the second reactor shifts with increasing pressure toward BDO. When operation is effected below the pressure range, mainly GBL is conveyed out of the second reactor and the recycle stream thus becomes uneconomically large.

The catalyst hourly space velocity of the inventive hydrogenation stages is in each case in the range from 0.02 to 2 kg of reactants of catalyst·hour. The catalyst hourly space velocity is preferably in the range from 0.05 to 1 kg of reactants of catalyst·hour. When the catalyst hourly space velocity is increased above the range specified in the case of MA as the feed, an increase in the proportion of SA and succinic acid in the hydrogenation effluent of the first reactor is generally observed. When the hourly space velocity is reduced below the minimum hourly space velocity, overhydrogenation products occur to an increased extent; moreover, the process becomes uneconomic owing to the low hourly space velocities.

The molar hydrogen/reactant ratio is likewise a parameter which has an important influence on the product distribution and also the economic viability of the process according to the invention. From an economic point of view, a low hydrogen/reactant ratio is desirable. The lower limit is at a value of 5, although higher molar hydrogen/reactant ratios of from 20 to 650 are generally employed. The use of the above-described inventive catalysts and also the compliance with the above-described temperature values allows the use of favorable, low hydrogen/reactant ratios in the hydrogenation of the first stage, which are preferably at values of from 20 to 200, preferably from 40 to 150. The favorable range is at values of from 50 to 100.

In the second hydrogenation reactor, GBL is converted to BDO. Here, the molar hydrogen/GBL ratio in the second hydrogenation stage is selected at values of from 20 to 1000, preferably from 50 to 400, in particular from 100 to 300. These molar ratios make it possible to discharge the heat of reaction which arises out of the reactor of the second stage by means of the cycle gas and without external heat removal.

In order to establish the molar hydrogen/reactant ratios used in accordance with the invention, a portion, advantageously the majority, of the hydrogen is circulated. To this end, a cycle gas compressor known to those skilled in the art is generally used. The amount of hydrogen consumed chemically by the hydrogenation is supplemented. In a preferred embodiment, a portion of the cycle gas is discharged in order to remove inert compounds, for example n-butane. The circulated hydrogen may also, optionally after preheating, be utilized to evaporate the reactant stream.

Together with the hydrogen cycle gas, all products are circulated which do not fully condense out, if at all, when the gas stream leaving the hydrogenation reactor is cooled. These are in particular THF, water and by-products such as methane and butane. The cooling temperature is from 0 to 60° C., preferably from 20 to 45° C.

A plurality of reactors may also be connected in parallel or in series. Useful reactor types are all apparatus suitable for heterogeneously catalyzed reactions and having a gaseous reactant and product stream. Preference is given to tubular reactors, shaft reactors or reactors having internal heat removal, for example tube bundle reactors. Particular preference is given to using tube bundle reactors in the first hydrogenation stage and shaft reactors in the second hydrogenation stage.

In principle, there may be intermediate feeding between the catalyst beds. Also possible is intermediate cooling between or in the catalyst beds or reactors. When two reactors having different temperature range are used, the GBL recycling may be between the two reactors. When fixed bed reactors are used, it is possible to dilute the catalyst with inert material.

For the process according to the invention, different catalysts are used in the two hydrogenation stages.

The inventive catalyst of the first hydrogenation stage has the feature that it is capable of making available mixtures of GBL and THF which are variable with regard to the product ratios obtainable by gas phase hydrogenation of MA, said mixtures being substantially SA-free. It has high stability and high stressability, so that reactivations can be omitted and reactor volume can be saved. All of these points make a process practiced with this catalyst particularly economically viable.

The inventive catalyst of the first hydrogenation stage has, as a main constituent, copper oxide and an acidic oxide material, and may optionally contain one or more further metals or compounds thereof, preferably oxides, from groups 1 to 14 (IA to VIIIA and IB to IVB of the old IUPAC nomenclature) of the Periodic Table of the Elements. When such a further oxide is used, preference is given to using $TiO_2$, $ZrO_2$, $SiO_2$, CaO, $Na_2O$, $Mn_2O_3$, BaO, and/or MgO.

The proportion of copper oxide in the overall composition of the catalyst is from 5 to 95% by weight, preferably at <70% by weight, more preferably from 10 to 65% by weight.

The inventive catalyst of the first hydrogenation stage comprises an acidic oxide which has to have a certain number of acidic sites. The required proportion of the oxide having acidic sites depends upon the amount of acidic sites contained therein. Suitable acidic oxides having a sufficient number of acidic sites are titanium dioxide, zirconium dioxide, silicon dioxide and aluminum dioxide, whose use is preferred, and mixed oxides of these oxides. Particularly preferred catalyst compositions have <70% by weight of copper oxide, in particular from 10 to 65% by weight of CuO, and >20% by weight, preferably >30% by weight, in particular from 35 to 90% by weight, of acidic oxide. Preference is given to low copper oxide contents also owing to the cost advantage achieved thereby. The acidic oxides allow high yields to be achieved. The metals of groups 1 to 14 of the Periodic Table of the Elements may be present in the catalyst in an amount of up to 30% by weight.

The catalysts of the first hydrogenation stage which are used may additionally contain one or more assistants in an amount of from 0 to 10% by weight. Assistants refer to organic and inorganic substances which contribute to improved processing during the catalyst preparation and/or to an increase in the mechanical stability of the shaped catalyst bodies. Such assistants are known to those skilled in the art; examples include graphite, stearic acid, silica gel, cellulose compounds, starch, polyolefins, carbohydrates (sugars), waxes, alginates and aluminum oxide, aluminum oxide hydroxide, for example in the form of boehmite; zirconium oxide, silicon oxide and their sols, substituted and unsubstituted siloxanes and copper powder.

The catalysts of the first hydrogenation stage can be prepared by methods known to those skilled in the art. Preference is given to processes in which the copper oxide is obtained finely divided and intimately mixed with the other constituents of the active composition and the acidic oxide. Particular preference is given to precipitating the metal salts and/or hydroxides in question from aqueous solution, and washing, drying and calcining them. Useful metal salts are, for example, nitrates, sulfates, carbonates, chlorides, acetates or oxalates. Subsequently, this starting material is processed to the shaped bodies by known methods, for example extruding, tableting or by agglomeration processes, if appropriate with addition of assistants.

It is also possible to prepare the inventive catalysts of the first hydrogenation stage by applying the active composition or precursor compounds of the active composition to an acidic oxide, for example by impregnation or vapor deposition. Inventive catalysts may also be obtained by reshaping a mixture of active components and acidic oxide or a precursor compound thereof with an oxide having acidic sites or a precursor compound thereof.

The catalysts of the first hydrogenation stage are used in the form of shaped bodies. Examples include extrudates, ribbed extrudates, other extrudate shapes, tablets, rings, spheres and spall.

Among all shaped bodies, particularly extrudates are suitable for the catalyst of the first hydrogenation stage. They are obtained by extruding the calcined starting compound with an assistant (binder), for example boehmite or p-boehmite (AlOOH) and subsequently calcined. The binder may be pretreated before extrusion. This is preferably effected with acid, for example with formic acid, nitric acid or hydrochloric acid. Other assistants, for example pore formers such as carboxymethylcellulose, potato starch or stearic acid may additionally be added before the extrusion.

The inventive volume of the shaped bodies of the first hydrogenation stage is determined by calculation from the dimensions of the shaped bodies.

For the second hydrogenation stage, a catalyst is utilized which has, as the catalytically active main constituent, copper oxide, and must only have a small number of acidic sites. When a catalyst is used which has too high a number of acidic sites, BDO is dehydrated to give THF.

A suitable oxide material which has a sufficiently small number of acidic sites is a material selected from the group of ZnO, $Al_2O_3$, $SiO_2$, $TiO_2$, $ZrO_2$, $CeO_2$, MgO, CaO, SrO, BaO, $La_2O_3$ and $Mn_2O_3$ and mixtures thereof. Preferred support materials are ZnO/$Al_2O_3$ mixtures, delta-, theta-, alpha- and eta-modifications of $Al_2O_3$, and mixtures which comprise $Al_2O_3$ and at least one component from the group of $SiO_2$, $TiO_2$, $ZrO_2$ on the one hand and from the group of ZnO, MgO, CaO, SrO and BaO on the other, or which contain at least one component from the group of $SiO_2$, $TiO_2$, $ZrO_2$ on the one hand and from the group of ZnO, MgO, CaO, SrO and BaO on the other. Particularly preferred support materials are pure ZnO, ZnO/$Al_2O_3$ mixtures in a weight ratio of from 100:1 to 1:2, and mixtures of $SiO_2$ with MgO, CaO and/or ZnO in a weight ratio of from 200:1 to 1:1.

The amount of copper oxide is at values of $\leq 95\%$ by weight, preferably from 5 to 95% by weight, in particular from 15 to 80% by weight; the oxide material is used in amounts of $\geq 5\%$ by weight, preferably from 5 to 95% by weight, in particular from 20 to 85% by weight.

Owing to the toxicity of chromium catalysts, preference is given to using chromium-free catalysts in both hydrogenation stages. It will be appreciated that corresponding chromium catalysts known to those skilled in the art are also suitable industrially for use in the process according to the invention, although this does not give rise to the desired advantages which are in particular of environmental and occupational nature.

The catalysts used for the second hydrogenation stage may additionally contain an assistant in an amount of from 0 to 10% by weight. Assistants refer to organic and inorganic substances which contribute to improved processing during the catalyst preparation and/or to an increase in the mechanical stability of the shaped catalyst bodies. Such assistants are known to those skilled in the art; examples include graphite, stearic acid, silica gel and copper powder.

The catalysts of the second hydrogenation stage can be prepared by methods known to those skilled in the art. Preference is given to processes in which the copper oxide is obtained finely divided and intimately mixed with the other constituents; particular preference is given to impregnation and precipitation reactions.

These starting materials may be processed to the shaped bodies by known methods, for example extrusion, tableting or by agglomeration processes, if appropriate with the addition of assistants.

Alternatively, inventive catalysts of the second hydrogenation stage may also be prepared, for example, by applying the active component to a support, for example by coating or vapor deposition. In addition, inventive catalysts may also be obtained by reshaping a heterogeneous mixture of active component or precursor compound thereof with a support component or precursor compound thereof.

The catalysts are preferably used in the form of shaped bodies. Examples include extrudates, ribbed extrudates, other extrudate shapes, tablets, rings, spheres and spall.

In the inventive hydrogenation in which, in addition to MA, other above-defined $C_4$ dicarboxylic acids or derivatives thereof may be used as a reactant, both catalysts (first and second hydrogenation stage) are used in reduced, activated form. The activation is effected using reducing gases, preferably hydrogen or hydrogen/inert gas mixtures, either before or after the installation into the reactor in which the process according to the invention is carried out. When the catalyst has been installed into the reactor in oxidic form, the activation may be carried out either before the start-up of the plant with the inventive hydrogenation or during the start-up, i.e. in situ. The separate activation before the start-up of the plant is generally effected using reducing gases, preferably hydrogen or hydrogen/inert gas mixtures, at elevated temperatures, preferably between 100 and 300° C. In the in situ activation, the activation is effected in the course of the running-up of the plant by contact with hydrogen at elevated temperature.

The BET surface area of both copper catalysts in the oxidic state is from 10 to 400 m$^2$/g, preferably from 15 to 200 m$^2$/g, in particular from 20 to 150 m$^2$/g. The copper surface area ($N_2O$ decomposition) of the reduced catalysts in the installed state is >0.2 m$^2$/g, preferably >1 m$^2$/g, in particular >2 m$^2$/g.

In one variant of the invention, catalysts are used for both hydrogenation stages which have a defined porosity. In the form of shaped bodies, these catalysts exhibit a pore volume of $\geq 0.01$ ml/g for pore diameters of >50 nm, preferably $\geq 0.025$ ml/g for pore diameters of >100 nm and in particular $\geq 0.05$ ml/g for pore diameters of >200 nm. In addition, the ratio of macropores having a diameter of >50 nm to the total pore volume for pores having a diameter of >4 nm is at values >10%, preferably >20%, in particular >30%. Often, use of these catalysts allows high THF yields and selectivities to be achieved. The porosities mentioned were determined by mercury intrusion to DIN 66133. The data evaluated were in the pore diameter range of from 4 nm to 300 μm.

The catalysts used in accordance with the invention for both hydrogenation stages generally have sufficient stability. In the case that the activity and/or selectivity of the catalyst should nevertheless fall in the course of its operating time, the catalyst may be regenerated by measures known to those skilled in the art. These preferably include reductive treatment of the catalyst in a hydrogen stream at elevated temperature. If desired, the reductive treatment may precede an oxidative treatment. In this case, the catalyst charge is flowed through at elevated temperature by the gas mixture comprising molecular oxygen, for example air. In addition, there is the possibility of washing the catalyst with a suitable solvent, for example ethanol, THF or GBL, and subsequently drying in a gas stream.

The process according to the invention has the feature that reactants to be hydrogenated and having differing purity may be used in the hydrogenation reaction. It will be appreciated that a reactant of high purity, especially MA, may be used in the hydrogenation reaction. However, the catalyst used in accordance with the invention and also the other reaction conditions selected in accordance with the invention also enable the use of reactants, especially MA, which are contaminated with the customary compounds occurring in the oxidation of benzene, butenes or n-butane, and also any further components. In a further embodiment, the inventive hydrogenation process may comprise a preceding stage which comprises the preparation of the reactant to be hydrogenated by partial oxidation of a suitable hydrocarbon stream and the removal of the reactant to be hydrogenated from the product stream obtained thereby.

In particular, this reactant to be hydrogenated is MA. Preference is given to using MA which stems from the partial oxidation of hydrocarbons. Suitable hydrocarbon streams are benzene, $C_4$ olefins (e.g. n-butenes, $C_4$ raffinate streams) or n-butane. Particular preference is given to using n-butane, since it constitutes an inexpensive, economically viable starting material. Processes for partially oxidizing n-butane are described, for example, in Ullmann's Encyclopedia of Industrial Chemistry, 6th Edition, Electronic Release, Maleic and Fumaric Acids—Maleic Anhydride.

The thus obtained reaction effluent is then taken up in a suitable organic solvent or solvent mixture which has a boiling point at least 30° C. higher than MA at atmospheric pressure.

This solvent (absorbent) is brought to a temperature between 20 and 160° C., preferably between 30 and 80° C. The maleic anhydride-containing gas stream from the partial oxidation may be contacted with the solvent in various ways: (i) passing the gas stream into the solvent (for example via gas injection nozzles or sparging rings), (ii) spraying the solvent into the gas stream and (iii) countercurrent contact between the gas stream flowing upward and the solvent flowing downward in a column having trays or packings. In all three variants, the apparatus known to those skilled in the art for gas absorption may be used. In the selection of the solvent to be used, care has to be taken that it does not react with the reactant, for example the MA used with preference. Suitable solvents are: tricresyl phosphate, dibutyl maleate, butyl maleate, high molecular weight waxes, aromatic hydrocarbons having a molecular weight between 150 and 400 and a boiling point above 140° C., for example dibenzylbenzene; dialkyl phthalates having $C_1$-$C_{18}$-alkyl groups, for example dimethyl phthalate; butyl phthalate, n-propyl or isopropyl phthalate; di-$C_1$-$C_4$-alkyl esters of other aromatic and aliphatic dicarboxylic acids, for example dimethyl 2,3-naphthalenedicarboxylate, dimethyl 1,4-cyclohexanedicarboxylate, alkyl phthalates having $C_1$-$C_8$-alkyl groups, for example methyl phthalate, ethyl phthalate, butyl phthalate, n-propyl and isopropyl phthalate; $C_1$-$C_4$-alkyl esters of other aromatic and aliphatic dicarboxylic acids, for example methyl 2,3-naphthalenedicarboxylate, methyl 1,4-cyclohexanedicarboxylate, methyl esters of long-chain fatty acids having, for example, from 14 to 30 carbon atoms, high-boiling ethers, for example dimethyl ethers of polyethylene glycol, for example tetraethylene glycol dimethyl ether.

Preference is given to using phthalates.

The solution resulting after the treatment with the absorbent generally has an MA content of from about 5 to 400 grams per liter.

The offgas stream remaining after the treatment with the absorbent comprises mainly the by-products of the preceding partial oxidation such as water, carbon monoxide, carbon dioxide, unconverted butanes, acetic acid and acrylic acid. The offgas stream is virtually free of MA.

Subsequently, the dissolved MA is driven out of the absorbent. This is effected with hydrogen at, or at a maximum of 10% above, the pressure of the subsequent hydrogenation or alternatively under reduced pressure with subsequent condensation of remaining MA. In the stripping column, a temperature profile is observed which results from the boiling points of MA at the top and the virtually MA-free absorbent at the bottom of the column at the particular column pressure and the dilution with carrier gas (in the first case with hydrogen) set.

In order to prevent losses of solvent, rectifying internals may be disposed above the feed of the crude MA stream. The virtually MA-free absorbent removed from the bottom is fed back to the absorption zone. The $H_2$/MA ratio is from about 20 to 400. Otherwise, the condensed MA is pumped into an evaporator and evaporated there into the cycle gas stream.

The MA-hydrogen stream still contains by-products which are formed in the partial oxidation of n-butane, butenes or benzene with oxygen-containing gases, and also absorbent which has not been removed. These are in particular acetic acid and acrylic acid as by-products, water, maleic acid and also the dialkyl phthalates which are used with preference as absorbents. The MA contains acetic acid in amounts of from 0.01 to 1% by weight, preferably from 0.1 to 0.8% by weight, and acrylic acid in amounts of from 0.01 to 1% by weight, preferably from 0.1 to 0.8% by weight, based on MA. In the hydrogenation stage, acetic acid and acrylic acid are fully or partly hydrogenated to ethanol and propanol respectively. The maleic acid content is from 0.01 to 1% by weight, in particular from 0.05 to 0.3% by weight, based on MA.

When dialkyl phthalates are used as absorbents, their content in the MA depends strongly upon the correct operation of the stripping column, especially of the rectifying section. In a suitable operating mode, phthalate contents of up to 1.0% by weight, in particular up to 0.5% by weight, should not be exceeded, since the consumption of absorbent otherwise becomes too high.

The thus obtained hydrogen/maleic anhydride stream is now fed to the first hydrogenation zone and hydrogenated. The catalyst activities and stabilities are virtually unchanged compared with the use of MA which has been highly prepurified, for example by distillation. The process according to the invention allows BDO yields which are at values of about 90%. High product selectivity is also achieved.

The process according to the invention will now be illustrated in detail in the examples which follow.

EXAMPLE 1

Preparation of an Inventive Spray Powder

In a heatable precipitation vessel equipped with a stirrer, 1.5 l of water are initially charged and heated to 80° C. In the course of one hour, a metal salt solution consisting of 877 g of $Cu(NO_3)_2*2.5H_2O$ and 1472 g of $Al(NO_3)_3*9H_2O$ in 2000 ml of water and simultaneously a 20% by weight sodium carbonate solution are metered into this precipitation vessel with stirring. The sodium carbonate metering is selected such that a pH of 6 is established in the precipitation vessel. On completion of addition of the metal salt solution, further sodium carbonate solution is added until a pH of 8 has been achieved in the precipitation vessel and stirring is continued at this pH for a further 15 min. The total consumption of sodium carbonate solution is 5.5 kg. The suspension formed is filtered off and washed with water until it no longer contains any nitrate (<25 ppm). The filtercake is slurried with water. The resulting slurry is sprayed at from 120 to 135° C.

EXAMPLE 2

Preparation of Small Shaped Bodies a) Tablets (1.5×2 mm)

Shaped body volume: 3.5 mm$^3$

The spray powder from example 1 is subsequently calcined at 600° C. The catalyst prepared contains 61% by weight of CuO and 39% by weight of $Al_2O_3$. The latter is mixed intensively with 3% graphite and compressed to tablets of size 1.5×2 mm. These tablets contain 59% by weight of CuO, 38% by weight of $Al_2O_3$ and 3% by weight of carbon.

b) Extrudates

Shaped body volume: 3.5-5.3 mm$^3$

Boehmite is incipiently etched using formic acid, mixed with spray powder from example 1 and, after addition of water, extruded in an extruder to give extrudates of length 3 mm having a diameter of 1.5 mm. The extrudates are subsequently dried and calcined at 600° C. The extrudates contain 50% by weight of CuO and 50% by weight of $Al_2O_3$.

EXAMPLE 3

Preparation of the Catalyst for the Second Hydrogenation Stage:

Preparation of the Support 450 g of $Al(NO_3)_3.9H_2O$ are added to 649 g of a well-stirred aqueous solution of zinc nitrate having a zinc content of 14.5% by weight and the mixture is brought to a volume of 1.25 l using water in order to bring the aluminum salt into solution (solution A). In a separate vessel, 474 g of anhydrous sodium carbonate are dissolved in water and the solution is made up to 2 l with water. (Solution B).

Solution A and solution B are heated at 50° C. and passed via separate lines into a precipitation vessel which contains a well-stirred solution of 20 g of $NaHCO_3$ in 350 ml of water heated to 50° C. Appropriate adjustment of the feed rates of solutions A and B brings the pH to 6.8 within approx. 3 minutes. While keeping the pH constant at 6.8 and the temperature at 50° C., the entire solution A is reacted with sodium carbonate. The suspension formed in this way is subsequently stirred for a further 3 hours, in the course of which the pH is kept at 6.8 by occasionally adding dilute nitric acid. The suspension is filtered and washed with distilled water until the nitrate content of the washing water is <10 ppm. The filtercake is dried at 120° C. for 16 h and subsequently calcined at 425° C. for 1 h.

Preparation of the Catalyst

A mixture of 432 g of a nitric acid solution of copper nitrate having a copper content of 15.5% by weight and 95 g of a nitric acid solution of zinc nitrate having a zinc content of 14.5% by weight is diluted with water to 500 ml and heated to 70° C. With stirring, 25.1 g of the above-described pulverulent calcined support are added gradually over approx. 5 minutes and the milky suspension obtained in this way is stirred for 15 minutes (suspension C).

In a separate vessel, 474 g of anhydrous sodium carbonate are dissolved in water and the solution is diluted to 2 l using water and heated to 70° C. (solution D). Suspension C and solution D are passed via separate lines into a precipitation vessel which is equipped with a stirrer and contains 350 ml of water heated to 70° C. Appropriate adjustment of the feed rates of suspension C and solution D brings the pH to 7.4.

While keeping the pH constant at 7.4 and the temperature at 70° C., the entire suspension C is reacted with sodium carbonate. The suspension formed in this way is subsequently stirred for a further 2 hours, in the course of which the pH is kept at 7.4 by occasionally adding dilute nitric acid or sodium carbonate solution D. The suspension is filtered and washed with distilled water until the nitrate content of the washing water is <10 ppm.

The filtercake is dried at 120° C. for 16 h and subsequently calcined at 430° C. for 1 h. The brown-black catalyst powder obtained in this way is mixed with 1.5% by weight of graphite and 5% by weight of copper powder (FFL No. 10914 from Norddeutsche Affinerie having a BET surface area of 0.23 $m^2/g$ and a particle size distribution in which 92% of the particles are in the 10 to 100 μm size range) and compacted to tablets of diameter 3 mm and height 3 mm. The tablets are finally calcined at 330° C. for 1 h. The catalyst prepared in this way has the chemical composition 66% CuO/24% ZnO/5% $Al_2O_3$/5% Cu.

EXAMPLE 4

Procedure of the MA Hydrogenation (1st Hydrogenation Stage) with the Inventive Catalyst from Example 2a)

a) Catalyst Activation

Before the start of the reaction, the catalyst is subjected to a hydrogen treatment in the hydrogenation apparatus at ambient pressure. To this end, the reactor is heated to 200° C. and the catalyst is activated with the particular specified mixture of hydrogen and nitrogen at atmospheric pressure for the time specified in table 1.

TABLE 1

| Time (minutes) | Hydrogen (l (STP)/h) | Nitrogen (l (STP)/h) |
| --- | --- | --- |
| 600 | 50 | 800 |
| 840 | 50 | 400 |
| 15 | 200 | 0 |

Subsequently, the catalyst is flushed with 200 l (STP)/h of hydrogen at 250° C. for 15 h.

b) Experimental Plant

The pressure apparatus used for the hydrogenation consists of an evaporator, a reactor, a condenser, a hydrogen feed, an offgas line and a compressor. The pressure in the apparatus is kept constant.

The molten MA is pumped from above through an inserted tube to the preheated (195° C.) evaporator and evaporated. A preheated mixture of fresh hydrogen and cycle gas passes into the evaporator from below. Example hydrogen and MA pass into the heated reactor filled with catalyst (diameter 20 mm). After the hydrogenation, the resulting mixture of GBL and THF together with water, other reaction products and hydrogen leaves the reactor and is precipitated in the condenser. A portion of the cycle gas is discharged, before the remainder, mixed with fresh hydrogen, re-enters the evaporator.

In this experimental plant, the reactor is filled with 1800 ml of the catalyst from example 2a (total mass 1575 g) and activated in accordance with 4a).

The condensed liquid reaction effluent, the offgas and the cycle gas are analyzed quantitatively by gas chromatography.

The operating parameters and experimental results can be taken from table 2.

TABLE 2

| Experiment | Pressure [bar] | Hourly space velocity [kgMA/lcath] | Temp. [° C.] | THF [mol %] | GBL [mol %] | Butanol [mol %] | SA [mol %] |
| --- | --- | --- | --- | --- | --- | --- | --- |
| 1 | 5 | 0.2 | 249 | 20.2 | 76.4 | 0.8 | 0.7 |
| 2 | 5 | 0.2 | 251 | 40.5 | 56.0 | 1.8 | 0.4 |
| 3 | 5 | 0.2 | 253 | 62.2 | 33.9 | 2.6 | 0 |
| 4 | 10 | 0.3 | 251 | 15.1 | 82.1 | 0.6 | 0.6 |
| 5 | 10 | 0.3 | 253 | 55.5 | 41.5 | 2.0 | 0.2 |
| 6 | 10 | 0.3 | 254 | 82.4 | 12.5 | 3.5 | 0.1 |
| 7 | 10 | 0.3 | 257 | 93.5 | 0.2 | 5.2 | 0 |
| 8 | 25 | 0.4 | 249 | 36.5 | 61.1 | 0.6 | 0.8 |
| 9 | 25 | 0.4 | 250 | 40.8 | 55.8 | 0.9 | 0.6 |
| 10 | 25 | 0.4 | 251 | 49.8 | 48.0 | 0.7 | 0.3 |
| 11 | 25 | 0.4 | 255 | 97.7 | 0 | 1.8 | 0 |

EXAMPLE 5

Procedure of the MA Hydrogenation (1st Hydrogenation Stage) with the Catalyst from Example 2b)

a) Catalyst Activation

Before start of the reaction, the catalyst is subjected to a hydrogen treatment in the hydrogenation apparatus at ambient pressure. To this end, the reactor is heated to 200° C. and the catalyst is activated with the particular specified mixture of hydrogen and nitrogen at atmospheric pressure for the time specified in table 3.

TABLE 3

| Time (minutes) | Hydrogen (l (STP)/h) | Nitrogen (l (STP)/h) |
| --- | --- | --- |
| 600 | 50 | 800 |
| 840 | 50 | 400 |
| 15 | 200 | 0 |

Subsequently, the catalyst is flushed with 200 l (STP)/h of hydrogen at 250° C. for 15 h.

b) Experimental Plant

The pressure apparatus used for the hydrogenation consists of an evaporator, a reactor, a condenser, a hydrogen feed, an offgas line and a compressor. The pressure in the apparatus is kept constant.

The molten MA is pumped from above through an inserted tube to the preheated (195° C.) evaporator and evaporated. A preheated mixture of fresh hydrogen and cycle gas passes into the evaporator from below. Example hydrogen and MA pass into the heated reactor filled with catalyst (diameter 34 mm). After the hydrogenation, the resulting mixture of GBL and THF together with water, other reaction products and hydrogen leaves the reactor and is precipitated in the condenser. A portion of the cycle gas is discharged, before the remainder, mixed with fresh hydrogen, re-enters the evaporator.

In this experimental plant, the reactor is filled with 1200 ml of the catalyst from example 2b and activated in accordance with 5a).

The condensed liquid reaction effluent, the offgas and the cycle gas are analyzed quantitatively by gas chromatography.

The operating parameters and experimental results can be taken from table 4.

TABLE 5

| Time (minutes) | Hydrogen (l (STP)/h) | Nitrogen (l (STP)/h) |
|---|---|---|
| 120 | 10 | 550 |
| 30 | 25 | 400 |
| 15 | 60 | 100 |
| 180 | 60 | 0 | c) Hydrogenation Apparatus:

The product effluent of experiment 9, example 4 is pumped into a preheated evaporator and evaporated there in counter-current with a mixture of hydrogen and cycle gas. The gaseous mixture of hydrogen and feed subsequently passes into the heated reactor. The reactor contains a mixture of glass rings and catalyst. After the hydrogenation, the reaction products and hydrogen leave the reactor. The reaction products are precipitated. A portion of the cycle gas is discharged, before

TABLE 4

| Experiment | Operating time [h] | Pressure [bar] | Hourly space velocity [kgMA/lcath] | Temp. [° C.] | THF [mol %] | GBL [mol %] | Butanol [mol %] | SA [mol %] |
|---|---|---|---|---|---|---|---|---|
| 12 | | | | | | | | |
| 13 | 1226 | 9 | 0.2 | 245 | 53.6 | 43.9 | 1.1 | 0 |
| 14 | 3081 | 9 | 0.2 | 246 | 53.4 | 42.8 | 2.1 | 0 |
| 15 | 3972 | 9 | 0.2 | 247 | 54.7 | 40.4 | 2.6 | 0.2 |

EXAMPLE 6

Procedure of the 2nd Hydrogenation Stage with the Catalyst from Example 3 (Feed: Product Effluent of Example 4, Experiment 9)

b) Catalyst Activation

Before the start of the reaction, the catalyst is subjected to a hydrogen treatment in the hydrogenation apparatus. To this end, the reactor is heated to 180° C. and the catalyst is activated with the particular specified mixture of hydrogen and nitrogen at atmospheric pressure for the time specified in table 1.

the remainder, mixed with fresh hydrogen, re-enters the evaporator.

The reactor of the hydrogenation apparatus described in example 1c is charged with 100 ml of the catalyst prepared in example 3 and 100 ml of glass rings. The activation is effected as described in example 6b. The reactant used is the product effluent of experiment 9, example 3 (55.8 area % GBL and 40.8 area % THF, 0.9 area % BuOH, 0.6 area % SA; or: 45.5% by weight of GBL, 25.9% by weight of THF, 0.6% by weight of SA, 0.5% by weight of BuOH, 0.4% by weight of butyric acid and 26% by weight of water based on the total mass). The reaction is carried out at different temperatures and different pressures. Table 6 summarizes the hourly space velocities and the results of the hydrogenation.

TABLE 6

| Experiment | Pressure [bar] | Hourly space velocity [kgMA/lcath] | Temp. [° C.] | THF [mol %] | GBL [mol %] | BDO [mol %] | Butanol [mol %] | SA |
|---|---|---|---|---|---|---|---|---|
| | 25 | 0.2 | 180 | 36.2 | 21.0 | 40.0 | 1.4 | 0 |
| | 25 | 0.3 | 180 | 40.8 | 33.7 | 23.0 | 1.8 | 0 |
| | 25 | 0.15 | 220 | 39.76 | 29.73 | 27.4 | 2.2 | 0 |
| | 25 | 0.3 | 220 | 41.5 | 37.8 | 18.0 | 2.0 | 0 |
| | 25 | 0.15 | 260 | 53.3 | 26.9 | 5.8 | 9.8 | 0 |
| | 25 | 0.3 | 260 | 47.0 | 38.2 | 7.8 | 4.9 | 0 |
| | 10 | 0.1 | 180 | 37.5 | 41.7 | 18.6 | 1.5 | 0 |
| | 10 | 0.1 | 220 | 43.5 | 47.4 | 5.9 | 3.4 | 0 |
| | 10 | 0.1 | 260 | 48.5 | 37.2 | 1.6 | 8.7 | 0 |

COMPARATIVE EXAMPLE 1

Preparation of the Comparative Catalyst 400 g of the active composition from example 1 are comminuted to a particle size of <1 mm, admixed with 3% by weight of graphite powder, mixed intensively and compacted to tablets of diameter 3 mm and height 3 mm. This catalyst has a volume of 21.2 mm$^3$.

COMPARATIVE EXAMPLE 2

Example 3 was repeated with the difference that 150 ml of the unsupported catalyst from comparative example 1 were used. The results of the catalytic test are reported in table 7.

TABLE 7

| Comparative example 2 | Pressure [bar] | Hourly space velocity [kgMA/lcath] | Temp. [° C.] | THF [mol %] | GBL [mol %] | Butanol [mol %] | SA [mol %] |
|---|---|---|---|---|---|---|---|
| | 5 | 0.2 | 253 | 36.6 | 38.8 | 3.0 | 16.0 |

What is claimed is:

1. A process for variably preparing mixtures of optionally alkyl-substituted butanediol (BDO), butyrolacetone (GBL) and tetrahydrofuran (THF) by two-stage hydrogenation in the gas phase of C$_4$ dicarboxylic acids and/or derivatives thereof, which comprises
   a) hydrogenating in a gas phase a gas stream of C$_4$ dicarboxylic acids and/or derivatives thereof over a catalyst at a pressure of from 2 to 100 bar and a temperature of from 200° C. to 300° C. in a first reactor in the presence of a noble metal-free catalyst in the form of shaped catalyst bodies having a volume of less than 20 mm$^3$, said catalyst from 5 to 95% by weight of oxide of copper and from 5 to 95% by weight of an oxide having acidic sites, to give a stream containing alkyl-substituted GBL and THF,
   b) removing any succinic anhydride (SA) formed by partial condensation,
   c) converting the products remaining predominantly in the gas phase in the partial condensation, THF, water and GBL, under the same pressure or under a pressure reduced by the pressure drops in the hydrogenation circuit and at a temperature of from 150 to 240° C., in a second reactor over a noble metal-free catalyst which ≦95% by weight of CuO and from 5 to 95% by weight of one or more oxides selected from the group of ZnO, Al$_2$O$_3$, SiO$_2$, TiO$_2$, ZrO$_2$, CeO$_2$, MgO, CaO, SrO, BaO, La$_2$O$_3$ and Mn$_2$O$_3$ to give a stream comprising a mixture of BDO, GBL and THF,
   d) removing the hydrogen from the products and recycling it into the hydrogenation,
   e) separating by distillation the products, THF, BDO, GBL and water, recycling a GBL-rich stream into the second reactor or discharging it, and working up BDO, THF and GBL by distillation,
   and setting the ratio of the products, THF, GBL and BDO, relative to one another within the range from 10 to 100% by weight of THF, from 0 to 90% by weight of GBL and from 0 to 90% by weight of BDO only by varying the temperatures in the two hydrogenation reactors and also the GBL recycle stream.

2. The process according to claim 1, wherein the partial condensation of the succinic anhydride is designed as a circulation quench cycle.

3. The process according to claim 1, wherein the evaporation of the recycled GBL or GBL/water mixture is effected in a countercurrent apparatus, with the GBL/THF-laden cycle gas hydrogen.

4. The process according to claim 1, wherein the partial condensation of the succinic anhydride and the evaporation of the GBL or GBL/water recycle stream are combined in one apparatus, and the succinic anhydride is discharged as the bottom effluent together with residual GBL, water and high-boiling secondary components.

5. The process according to claim 1, which is carried out continuously.

6. The process according to claim 1, wherein the inlet temperature in the first reactor is at values of from 200° C. to 300° C., and from approx. 5 to 15° C., below the hotspot temperature.

7. The process according to claim 1, wherein the temperature increase in the second reactor is not more than 90° C.

8. The process according to claim 1, wherein the inlet temperature in the second reactor is at values between 150° C. and 270° C.

9. The process according to claim 1, wherein both hydrogenation stages are carried out at pressures of from 2 to 100 bar.

10. The process according to claim 1, wherein the catalyst hourly space velocity of the first hydrogenation stage is in the range from 0.02 to 2 kg of reactant/l of catalyst hour.

11. The process according to claim 1, wherein the catalyst hourly space velocity of the second hydrogenation stage is in the range from 0.02 to 2 kg of reactant/l of catalyst·hour.

12. The process according to claim 1, wherein the molar hydrogen/reactant ratio in the first hydrogenation stage is at values of from 20 to 650.

13. The process according to claim 1, wherein the molar hydrogen/GBL ratio in the second hydrogenation stage is at values of from 20 to 1000.

14. The process according to claim 1, wherein the reactor used in the first hydrogenation stage is a fixed bed reactor, a shaft reactor, a fluidized bed reactor or a reactor having internal heat removal.

15. The process according to claim 1, wherein the reactor used in the second hydrogenation stage is a fixed bed reactor, a tube bundle reactor, a fluidized bed reactor or a reactor having internal heat removal.

16. The process according to claim 1, wherein the volume of the individual shaped body in the first hydrogenation stage is <10 mm$^3$.

17. The process according to claim 1 wherein the CuO is less than 80% by weight, and is more than 20% by weight, of an oxide having acidic sites present.

18. The process according to claim 1, wherein the oxide having acidic sites is Al$_2$O$_3$.

19. The process according to claim 1, wherein the catalyst of the first hydrogenation stage is one or more metals or a compound thereof, from the group consisting of the elements of groups 1 to 14 of the Periodic Table of the Elements.

20. The process according to claim 1, wherein the catalyst is in the form of an extradite.

21. The process according to claim 1, wherein the catalyst of the second hydrogenation stage, in addition to CuO, oxides selected from the group of $ZnO/Al_2O_3$ mixtures, delta-, theta-, alpha- and eta-modifications of $Al_2O_3$, and mixtures which comprise $Al_2O_3$ and at least one component from the group of $SiO_2$, $TiO_2$, $ZrO_2$ on the one hand and from the group of ZnO, MgO, CaO, SrO and BaO on the other, or which contain at least one component from the group of $SiO_2$, $TiO_2$, $ZrO_2$ on the one hand and from the group of ZnO, MgO, CaO, SrO and BaO on the other.

22. The process according to claim 1, wherein the catalyst of the second hydrogenation stage comprises oxides selected from ZnO, $ZnO/Al_2O_3$ mixtures in a weight ratio of from 100:1 to 1:2 and mixtures of $SiO_2$ with MgO, CaO and/or ZnO in a weight ratio of from 200:1 to 1:1.

* * * * *

UNITED STATES PATENT AND TRADEMARK OFFICE
CERTIFICATE OF CORRECTION

PATENT NO. : 7,442,810 B2 Page 1 of 1
APPLICATION NO. : 10/581074
DATED : September 9, 2008
INVENTOR(S) : Swaminathan Venkataraman It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 99 days Delete the phrase "by 99 days" and insert -- by 175 days --

Signed and Sealed this

Seventh Day of July, 2009

JOHN DOLL
*Acting Director of the United States Patent and Trademark Office*